United States Patent [19]

Seubert et al.

[11] Patent Number: 4,918,059

[45] Date of Patent: Apr. 17, 1990

[54] LOW MOLECULAR WEIGHT ALKALI METAL HUMINATES, METHOD FOR THEIR PREPARATION AND APPLICATIONS THEREOF

[75] Inventors: Bernhard Seubert, Edingen-Neckarhausen; Helmut Beilharz, Schriesheim; Werner Fickert, Mannheim; Gunter Jeromin, Heidelberg; Ulrich Spitaler, Freinsheim, all of Fed. Rep. of Germany

[73] Assignee: Rutgerswerke AG, Fed. Rep. of Germany

[21] Appl. No.: 162,741

[22] Filed: Mar. 1, 1988

[30] Foreign Application Priority Data

Mar. 12, 1987 [DE] Fed. Rep. of Germany ....... 3707909

[51] Int. Cl.$^4$ ...................... A61K 31/70; C07H 15/00
[52] U.S. Cl. ...................................... 514/33; 536/17.3
[58] Field of Search ........................ 514/33; 536/17.3

[56] References Cited

PUBLICATIONS

Kingzett's Chemical Encyclopedia, 9th ed. (London), p. 483, 1969.
Chemical Abstracts 104:6219r (Liogonkii et al.) 1916.
Chemical Abstracts 105:171313v (Adhikari et al.) 1986.
Chemical Abstracts 103:98707d (Zeng et al.) 1985.
Balabanoua-Radonova et al., Fuel, 1981, vol. 60, pp. 685-88.
Curuetto et al., Plant & Soil, 66, 205-15, 1982.

*Primary Examiner*—Leonard Schenkman
*Attorney, Agent, or Firm*—Bierman and Muserlian

[57] ABSTRACT

Alkali metal or ammonium salts of humic acids, referred to as alkali metal huminates of low molecular weight, obtained by slurrying humic-containing matter in alkaline or ammoniacal aqueous solutions, separating the resulting suspension from coarse solid matter and, through centrifugation, freeing the solution from extremely fine solid materials and high molecular weight huminates. The resulting solution is neutralized and buffered at a pH value ranging from 6.2 to 7.2, and is again purified through centrifugation. From this solution, a low molecular weight fraction is separated. The resulting alkali metal huminates of low molecular weight are useful as therapeutic agents in wound healing and for use in highly effective synthetic mud baths.

7 Claims, No Drawings

LOW MOLECULAR WEIGHT ALKALI METAL HUMINATES, METHOD FOR THEIR PREPARATION AND APPLICATIONS THEREOF

STATE OF THE ART

Humic acids are mixtures of organic, high molecular weight compounds having similar structures, the molecular weights of which are described in literature as being in a range of 200 to more than 200,000.

Healing properties have been ascribed to these humic acids and generally humic substances found in moors, peat and colored clay or in humic matter containing water (see Ziechmann, Therapiewoche 28 (1978), 1199–1211). Ziechmann, Huminstoffe (Humic Matter), Publisher Chemie 1980, at page 223, describes various methods for separating humic acids, including ultracentrifugation, column chromatography, or analytically with different organic solvents into different fractions differing in molecular weights. However, humic acids and salts thereof are considered parenterally toxic (see Kuhnert et al, Arch. exper. Vet. med. 36 (1982), 169–177). For this reason, humic substances, except for moor baths, have heretofore been used primarily in veterinary medicine.

OBJECTS OF THE INVENTION

It is therefore an object of the invention to provide novel humic substances which are parenterally significantly less toxic, the preparation of which has uniform pharmaceutical efficacy and which has long-term storability, and consequently can be safely used in human medicine.

This and other objects and advantages of the invention will become obvious from the following detailed description.

THE INVENTION

It has now been found, that in preparing a specific alkali metal aqueous extract of humic matter, a fraction of alkali metal huminates can be obtained which has good healing properties, and a parenteral toxicity significantly lower than that of the previously available huminates. The huminates of this fraction have a median relative molar mass of 1,000 grams per mole ranging from 300 to 1,500 grams per mole.

Surprisingly, this fraction of low molecular weight alkali metal huminates has an additional advantage in that it is stable. Although humic acids and huminates normally are subject to a continuous humification process, that is, steadily continue to further polymerize, and although low molecular humic matter is considered particularly reactive in this respect, even after long-term storage, the alkali metal huminate fraction of the invention shows no tendencies to further polymerize.

Starting material for the huminates of the invention include all humic matter-containing products, for example, peat, mud, brown coal, colored clays, or humic matter-containing water and its humus mud. These humic acid-containing, preferably high-concentration humic acid-containing substrates with contents of at least 5 and not more than 50 percent humic acid, are slurried in water and mixed with an alkali metal solution or ammonium hydroxide solution. Alternatively, they are directly mixed with an alkali metal solution or ammonium hydroxide solution. Any alkali metal hydroxide can be used. However, for reasons of cost-efficiency, potassium or sodium hydroxide are preferred.

The quantity of the alkali metal solution or ammonium hydroxide is not critical. It should, however, be sufficient to render the pH value of the originating suspension in a region between 8 and 9.

Preparation of this alkali metal suspension must be carried out with care because the mixture tends to foam. It is therefore favorable to mix the substrate into the alkali metal solution at a slightly increased temperature, approximately 25°–40° C. As soon as the tendency to foam has died down, the suspension is heated to a temperature in the range of 45°–60° C., and stirred at this temperature for at least 24 hours, preferably 48–72 hours. Subsequently, the mixture is allowed to stand at room temperature for 2–8, preferably 4–6 weeks, wherein the undissolved particles, sediment and the supernatant is decanted or filtered off. The same effect can alternatively be achieved through coarse centrifugation (1,000 to 5,000 xg). The resultant solution is subsequently purified further in a suitable centrifuge at approximately 10,000 to 30,000 xg and is thereby freed of the finest solid particles and higher molecular weight huminates.

The centrifuged substance is neutralized by the addition of acid or with acidic ion exchange (pH 7), and subsequently brought to a pH value in the range of 6.2 to 7.2 with a suitable buffer (for example, phosphate-, tris-, citric acid). Further humic matter fractions are precipitated, in particular those which can be precipitated with acid. The solution is then centrifuged at about 10,000 to 30,000 xg.

Then, the huminate solution, purified and freed of high molecular humic matter, is at this point again fractionated by any known means, including ultracentrifuge, preparatory HPLC, column or gel chromatography. The preferred fractionation method is electrodialysis which can be carried out either as low (20 to 400 V) or high voltage (5 to 250 KV) electrodialysis.

The fraction of the invention is of low molecular weight, has electrical charges, and is therefore transported in the electrode chambers of the electrodialysis device. Subsequent purification of the desired fraction can, if necessary, take place through additional ultrafiltration with filters with separating limits ranging from 5,000 to 1,000 D.

In the following examples there are described several preferred embodiments to illustrate the invention. However, it should be understood that the invention is not intended to be limited to the specific embodiments.

EXAMPLES

EXAMPLE I

In an alkali resistant agitator, 100 liters of demineralized water (conductivity: below 5 micro s/cm, pH 5–7) and 7.7 kg of 50% sodium hydroxide (DAB 8) were mixed and to this solution, 10 kg of peat were added at a temperature of 35° to 40° C. over a period of one hour. As soon as the tendency to foam died down, the mixture was carefully heated to 50° C. and held at this temperature while stirring for 48 hours. Then, the mixture was allowed to stand air sealed for 4 weeks at room temperature and was subsequently filtered through a filter of 0.5 mm pore size. The filtered solution was purified in a Westfalia separator using a solid jacket chamber drum at approximately 20,000 xg.

The centrifuged solution was adjusted to a pH of 6.5 by the addition of orthophosphoric acid (DAB 7), simultaneously buffered in the process, and then centrifuged again at approximately 20,000 xg. From this solution in an electrodialysis device which was equipped with a membrane of 0.025 um of sintered glass by applying a direct voltage of 200 V, the fraction (1) of the invention was obtained in the anode chamber as a 5–8% brown solution. The residue of dialysis was continuously transferred by pumping to avoid concentration polarizations. On the basis of the electrophoretic migration rate, a mean molecular weight of 1,000 with a spread of 300 to 1,500 was determined for the separated huminates of the invention. The following values were controlled while the dialysis was running: pH value: 6.4 to 6.8, microdialysis test: negative. When checking the stability after 60 days of alternating stress at 65/4° C. in a 12/12 hour rhythm, no changes of the parameters content, pH value, oxidation/reduction potential, and microdialysis test could be determined beyond random deviations.

EXAMPLE 2

In an alkali resistant agitator, 100 liters of demineralized water (conductivity: below 5 micro s/cm; pH value 5–7) and 8 liters of concentrated ammonia solution were mixed. 10 kg of healing clay were added to this solution over a period of 1 hour at a temperature of 35° C. to 40° C. As soon as the tendency to foam had subsided, the mixture was carefully heated to 50° C. and maintained at this temperature for 48 hours while stirring. Then, the mixture was air sealed and allowed to stand for 4 weeks. Afterwards, the solution was filtered through a filter of 0.5 mm pore size and the filtered solution was purified in a Westfalia separator using a solid jacket chamber drum at approximately 20,000 xg.

The centrifuged solution was adjusted to a pH of 7.0 by the addition of a strongly acidic ion exchange resin and, after filtration of the resin, brought to a pH of 6.8 by adding ammonium citric acid buffer and buffered and then again centrifuged at approximately 20,000 xg. Analogously to example 1, the fraction (2) of the invention was obtained from the resulting solution through electrodialysis. The obtained solution was highly purified by filtration through a filter with a separating limit of 5,000–1,000 D. During stability tests after 60 days of alternating stress of 56/4° C. every 12 hours, no changes of the parameters content, pH value, oxidation-reduction potential and microdialysis test beyond random deviations could be detected.

EXAMPLE 3

With the fractions (1) and (2) of Examples 1 and 2, the investigations described below were carried out and the listed results were obtained.

Toxicity:
By injecting the 1% solution into test animals (mice), the following values for the $LD_{50}$ were obtained.

|  | Fraction (1) (mg/kg) | Fraction (2) (mg/kg) |
| --- | --- | --- |
| subcutaneous | 1280 | 1115 |
| intraperitoneal | 828 | 770 |
| intravenous | 670 | 718 |

Stability:

After air sealed storage for 6 months at 23° C. upon performing the tests listed under examples 1 and 2, no changes were detectable.

Therapeutic effect:
Fibroplastin test

A culture of L-cells (mouse fibroblasts) treated with trypsine and brought into suspension were mixed with 50 ppm of low molecular weight alkali metal huminate. The culture was incubated for 48 hours at 37° C. using a commercially available nutrient medium. As a comparative test, an analogous culture without alkali metal huminate was also incubated. Subsequently, the number of viable cells in both cultures were determined. In the culture mixed with the low molecular weight alkali metal huminates, the number of viable cells was approximately 30% greater than in the control culture.

Wound healing:

A microdermatome superficial wound approximately 50 $mm^2$ in area and involving only the uppermost epithelial layers were incurred on two groups of hairless mice. In ten of these mice, the wound was wetted once with a 1% solution. The other mice remained untreated. During the observation time of 7 days, the following could be observed: Compared to the untreated mice, the wound area decreased more rapidly, and the wound dried earlier, in the treated mice, granulation started sooner, and the wound became cleaner sooner. Overall, healing could be observed 2 to 3 days earlier than in the control animals.

Various modifications of the process of the invention may be made without departing from the spirit or scope thereof and it should be understood that the invention is intended to be limited only as defined in the appended claims.

What we claim is:

1. Alkali metal and ammonium salts of humic acids with an average molecular weight of 1,000, the molecular weights of said salts ranging between 300 and 1500.

2. A method of preparing the salts of claim 1 comprising forming a slurry of humic-containing matter in an alkali metal or ammoniacal aqueous solution to form a suspension, separating the resulting suspension from coarse solid matter and centrifuging the latter to obtain a solution free of solid matter and high molecular weight huminates, neutralizing said solution and adjusting to a pH value between 6.2 to 7.2 with a buffer and centrifuging the said solution and separating from the solution the low molecular weight huminates of claim 1.

3. The method of claim 2 wherein centrifugation is carried out before and after precipitation with acid at approximately 10,000 to 30,000 xg.

4. The method of claim 2 wherein the separation of said low molecular weight huminates is performed with low and/or high voltage electrodialysis.

5. The method of claim 2 wherein a final high purification of the low molecular weight huminates is performed by filtration through a filter with a separating limit of 5,000 to 1,000 D.

6. A wound healing composition comprising an amount of a huminate of claim 1 sufficient to increase the healing rate and an inert pharmaceutical carrier.

7. A method of increasing the healing rate of a wound in a warm blooded animal comprising applying to the wound of a warm blooded animal an amount of an alkali metal huminate of claim 1 sufficient to increase the healing rate.

* * * * *